US 9,151,769 B2

(12) United States Patent
Hammond et al.

(10) Patent No.: US 9,151,769 B2
(45) Date of Patent: Oct. 6, 2015

(54) AUTOMATED CALIBRATION METHOD AND SYSTEM FOR A DIAGNOSTIC ANALYZER

(75) Inventors: Jeremy Hammond, Gorham, ME (US); Dominic Pelletier, Raymond, ME (US); Jason Aguiar, Portland, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 446 days.

(21) Appl. No.: 13/548,769

(22) Filed: Jul. 13, 2012

(65) Prior Publication Data

US 2013/0006566 A1    Jan. 3, 2013

Related U.S. Application Data

(63) Continuation-in-part of application No. 12/932,192, filed on Feb. 18, 2011, now Pat. No. 8,645,306.

(60) Provisional application No. 61/398,920, filed on Jul. 2, 2010.

(51) Int. Cl.
*G06F 19/00* (2011.01)
*G01N 35/00* (2006.01)

(52) U.S. Cl.
CPC ............ *G01N 35/00693* (2013.01); *G01N 2035/00702* (2013.01)

(58) Field of Classification Search
None
See application file for complete search history.

(56) References Cited

U.S. PATENT DOCUMENTS

| | | | |
|---|---|---|---|
| 5,485,550 A * | 1/1996 | Dalton | 706/52 |
| 6,421,553 B1 * | 7/2002 | Costa et al. | 600/476 |
| 7,047,144 B2 * | 5/2006 | Steiner | 702/64 |
| 7,734,400 B2 * | 6/2010 | Gayme et al. | 701/54 |
| 7,761,239 B2 * | 7/2010 | Chen et al. | 702/19 |
| 8,645,306 B2 * | 2/2014 | Hammond | 706/52 |
| 2002/0019722 A1 * | 2/2002 | Hupkes et al. | 702/181 |
| 2002/0095075 A1 * | 7/2002 | Madarasz et al. | 600/310 |
| 2004/0053333 A1 * | 3/2004 | Hitt et al. | 435/7.1 |
| 2004/0058372 A1 * | 3/2004 | Hitt et al. | 435/6 |
| 2004/0241669 A1 * | 12/2004 | Ghosh | 435/6 |
| 2005/0021212 A1 * | 1/2005 | Gayme et al. | 701/99 |

(Continued)

FOREIGN PATENT DOCUMENTS

WO    WO 2005060608 A2 *    7/2005

OTHER PUBLICATIONS

Ye, et al., "Performance Evaluation and Planning for Patient-Based Quality Control Procedures," Am J Clin Pathol, 2000; 113, pp. 240-248.

(Continued)

*Primary Examiner* — Kakali Chaki
*Assistant Examiner* — Fuming Wu
(74) *Attorney, Agent, or Firm* — Gerald T. Bodner

(57) ABSTRACT

An automated method for calibrating in real time a diagnostic analyzer includes the steps of receiving diagnostic results of patient samples calculated by the analyzer using pre-set parameters of the analyzer, and calculating the centroid of the analyzer's diagnostic results. The centroid of the analyzer's diagnostic results is subtracted from a centroid of diagnostic results of a field population of comparable analyzers to obtain a bias in the centroid of the analyzer's diagnostic results. The bias is compared to predetermined limits. Should the bias fall outside the predetermined limits, an optimization factor is derived and applied to the analyzer's diagnostic results to obtain optimized results from the analyzer without changing the pre-set parameters of the analyzer.

21 Claims, 6 Drawing Sheets

(56) References Cited

U.S. PATENT DOCUMENTS

| | | | |
|---|---|---|---|
| 2005/0209786 A1* | 9/2005 | Chen et al. | 702/20 |
| 2006/0083428 A1* | 4/2006 | Ghosh et al. | 382/224 |
| 2006/0158402 A1* | 7/2006 | Nathan et al. | 345/82 |
| 2006/0173628 A1* | 8/2006 | Sampas et al. | 702/19 |
| 2007/0055151 A1* | 3/2007 | Shertukde et al. | 600/437 |
| 2007/0134681 A1* | 6/2007 | Liew et al. | 435/6 |
| 2007/0191740 A1* | 8/2007 | Shertukde et al. | 600/586 |
| 2007/0239003 A1* | 10/2007 | Shertukde et al. | 600/437 |
| 2008/0201095 A1* | 8/2008 | Yip et al. | 702/85 |
| 2009/0181008 A1* | 7/2009 | Ray et al. | 424/130.1 |
| 2010/0332125 A1* | 12/2010 | Tan et al. | 701/207 |
| 2011/0276342 A1* | 11/2011 | Kazmierczak | 705/2 |
| 2011/0319746 A1* | 12/2011 | Kochba et al. | 600/407 |
| 2012/0005150 A1* | 1/2012 | Hammond | 706/52 |
| 2012/0115743 A1* | 5/2012 | Davicioni et al. | 506/9 |
| 2013/0006566 A1* | 1/2013 | Hammond et al. | 702/104 |

OTHER PUBLICATIONS

Westgard, et al., "*Quality Assurance*", Fundamentals of Clinical Chemistry, Third Edition, W. B. Saunders Company, 1987, pp. 249-251.

Beckman Coulter, "*XM-Exponentially Weighted Moving Average*", Beckman Coulter Technical Information Bulletin No. 9611, 2006, United States.

Flatland, et al., "*ASVCP quality assurance guidelines: control of general analytical factors in veterinary laboratories,*" Vet Clin Pathol 39/3, 2010, pp. 264-277.

Cembrowski, George S., "*Thoughts on quality-control systems: a laboratorian's perspective,*" Clinical Chemistry 43:5, 1997, pp. 886-892.

Westgard J.O., et al. "*A Multi-Rule Shewhart Chart for Quality Control in Clinical Chemistry*", Clinical Chemistry, vol. 27, No. 3, 1981, pp. 493-501.

Koch, et al. "*Selection of Medically Useful Quality-Control Procedures for Individual Tests Done in a Multitest Analytical System*", Clinical Chemistry, vol. 36, No. 2, 1990, pp. 230-233.

Lunetzky, et al., "*Performance characteristics of Bull's multirule algorithm for the quality control of multichannel hematology analyzers*", American Journal of Clinical Pathology, Nov. 1987 88(5): 634-8.

Baker, et al., "*Veterinary Hematology and Clinical Chemistry*", Ames, IA:Blackwell Publishing; 2006, pp. 17 and 84.

Simon Haykin, "*Neural Networks; A Comprehensive Foundation*", 2nd Edition, 1998, New York, NY, Macmillan College Publishing, 1998, pp. 83-85.

Yen, et al., "*Fuzzy Logic: Intelligence, Control, and Information, I/e*", Prentice Hall Engineering/Science/Mathematics, Upper Saddle River, NJ, Prentice Hall; 1998.

Meinkoth, et al., "*Normal Hematology of the Dog*", Schalm's Veterinary Hematology, Fifth Edition, Lippincott Williams & Wilkins, NY 2000, Chapter 163, pp. 1057-1059.

Bull, et al., "A Study of Various Estimators for the Derivation of Quality Control Procedures from Patient Erythrocyte Indices", Am. J. Clin. Pathol. 1974; vol. 61:473-481.

Koepke, et al., "Calibration and Quality Control of Automated Hematology Analyzers; Proposed Standard", Clinical and Laboratory Standards Institute, Apr. 1999, vol. 19, No. 7.

Grant, et al., "The Central Limit Theorem", Statistical Quality Control, 6th Edition, p. 201, The McGraw-Hill Companies, Inc., Boston, Massachusetts, Burr Ridge, Illinois, Dubuque Iowa, Madison, Wisconsin, New York, New York, San Francisco, California, St. Louis Missouri, 1996.

\* cited by examiner

AUTOMATED CALIBRATION METHOD AND SYSTEM FOR A DIAGNOSTIC ANALYZER

CROSS-REFERENCE TO RELATED APPLICATIONS

This application is a continuation-in-part of U.S. patent application Ser. No. 12/932,192, which was filed on Feb. 18, 2011, and is entitled "Automated Calibration Method and System for a Diagnostic Analyzer", the disclosure of which is incorporated herein by reference and on which priority is hereby claimed, which prior application is based on U.S. Provisional Application Ser. No. 61/398,920, which was filed on Jul. 2, 2010, and is entitled "Automated Calibration Method and System for a Diagnostic Analyzer", the disclosure of which is hereby incorporated by reference and on which priority is hereby claimed.

BACKGROUND OF THE INVENTION

1. Field of the Invention

The present invention generally relates to diagnostic instruments for human and veterinary applications, and more specifically relates to methods and systems for calibrating such instruments.

2. Description of the Prior Art

Diagnostic instruments have been used for decades in both the human and veterinary markets. These instruments include hematology analyzers, blood chemistry analyzers and other instruments that determine certain physiological properties of patients. In the veterinary market, the VetTest® chemistry analyzer and the VetAutoread™ automated hematology analyzer have been available since at least the 1990's. Some analyzers, like the VetAutoread™ hematology analyzer manufactured by IDEXX Laboratories, Inc. of Westbrook, Me., (see, www.idexx.com), utilize a fixed optical reference to determine instrument performance. Other analyzers, like the IDEXX LaserCyte® hematology analyzer, incorporate polymers with fixed size and index of refraction to ensure optical performance referred to as Qualibeads™. In addition, some analyzers, like the Sysmex XT-V manufactured by Sysmex Corp. of Hyogo, Japan, (see, www.sysmex.com), utilize a fixed cell control material to ensure assay performance. The veterinary market is very cost sensitive and controls are not run in the same manner as in human practices, which generally run fixed cell controls approximately at least once per 8-hour shift. In addition, for veterinary applications, species specific concerns arise since each species may have a different response to the system chemistry and different algorithms are often employed by species. Therefore, alternative methods are required to ensure instrument performance.

Patient-based approaches have been proposed, such as described in the aforementioned pending U.S. patent application Ser. No. 12/932,192, that provide a means to trend patient data in batches to reduce the impact of individual patient responses. The batches can then be evaluated in a control chart utilizing control chart rules to determine if the system has moved out of control. Fuzzy Logic approaches can then be used to define system optimization adjustments that bring the system back into control. This approach has the inherent benefit that the analyses are performed with patient data on a species-specific basis. This approach can run into difficulties if there are external factors that cause system shifts, such as reagent lot changes. Alternative approaches are required to handle patient sample data sets that are convoluted with reagent lot variability.

OBJECTS AND SUMMARY OF THE INVENTION

It is an object of the present invention to provide an automated system and method for optimizing a diagnostic instrument, such as a blood chemistry analyzer, in real time.

It is another object of the present invention to provide a system and method for calibrating a chemistry analyzer which automatically employ a species and lot-specific algorithm on patient samples to monitor the performance of the analyzer and through feedback adjust the parameters of the analyzer to maintain the analyzer within its calibration specifications.

It is yet another object of the present invention to provide a system and method for automatically calibrating a human or veterinary diagnostic instrument, such as a chemistry analyzer, based on patient samples using a centroid algorithm coupled with field population data for each species and lot supported.

It is a further object of the present invention to provide an automated system and method for calibrating a diagnostic analyzer which overcome the inherent disadvantages of known analyzer calibration systems and methods.

In accordance with one form of the present invention, a system and method for automated, real-time calibration of a diagnostic instrument, which includes but is not limited to a hematology analyzer, such as the aforementioned LaserCyte® analyzer or the ProCyte Dx® analyzer, each of which is manufactured by IDEXX Laboratories, Inc., or a dry reagent test slide chemical analyzer, such as the Catalyst DX® analyzer, also manufactured by IDEXX, to name a few (collectively referred to herein as "diagnostic analyzers"), used for veterinary or human applications, receive the diagnostic (e.g., chemistry) results of patient samples calculated by the analyzer using the analyzer's pre-set parameters (such as optical gain, for example), and apply a centroid calculation algorithm to the patient sample diagnostic results to obtain species and lot-specific centroid (median) values. Then, population data is gathered from other instruments running the same species and lots to determine target population centroids. Comparison of the specific instrument centroid to the population target centroid provides a measure of specific instrument accuracy bias to the population. If the accuracy bias does not exceed a predetermined threshold, then no optimization factor (or factors) is applied to the patient sample diagnostic results calculated by the analyzer using its pre-set parameters (e.g., optical gain).

However, should the accuracy bias exceed a predetermined threshold, then the method and system of the present invention apply an optimization factor (or factors) to the patient sample diagnostic results to obtain adjusted diagnostic results of the patient samples which are now within acceptable limits or ranges. Such adjusted diagnostic results are read out or displayed by the analyzer and represent a more accurate calculation of the patient sample diagnostic results.

The one or more optimization factors are derived from the application of optimization logic to the instrument reported centroid. The optimization logic includes finding the population centroid for the particular lot and animal species being tested and determining the bias from the instrument centroid, and then aggregating over multiple lots for the species to determine a lot-independent bias.

For many chemistry analyzers, the reagent test slides used therein have lots associated with them, and the analyzers have calibration curves associated with each of the lots. Therefore, the response of the chemistry analyzers may be different from one lot to another. A lot-specific field population centroid may be predetermined and used in the calculation of the bias in the diagnostic results for a particular analyzer. Alternatively, the field population centroids of several lots may be aggregated, such as by calculating their differences, or deltas, and the average of the lots, to determine a global field population centroid that is not lot-specific and which may be applied to a particular chemistry analyzer to derive a correction factor for compensating the analyzer's bias in its computation of a diagnostic results. It is preferred to use a global field population centroid rather than a lot-specific field population centroid, since a diagnostic analyzer may run through an entire lot of test slides in about one month.

The optimization factor (or factors) is used in modifying the calculations performed by the analyzer with its pre-set parameters to correct the results of such calculations without the need to actually change the analyzer's pre-set parameters stored in the analyzer's memory. Thus, for example, by applying the derived optimization factor, the overall gain to the analyzer's optical system may be effectively adjusted from 1.03 to 1.04 to more accurately provide patient sample diagnostic results read out or displayed by the analyzer. The optimization factor may be, for example, a multiplying factor, or an offset or additive factor.

The calibration method is preferably applied each time the diagnostic analyzer generates patient sample results so that the calculated results may be automatically adjusted in real time, and the optimization factor (which is applied to the analyzer's pre-set parameters) may be continually changed as is required, in order to provide more accurate patient readings.

In use, particularly when running human analyzers, the user could be alerted that an adjustment is likely needed. The user can then allow the adjustment and follow-up with a control fluid test to ensure the adjustment was proper, i.e. before running additional samples. For veterinary applications, adjustments can be made automatically. Also, in the veterinary field, targets and ranges are typically species specific, e.g. dogs, cats, horses.

A system which implements the automated calibration method of the present invention can be realized by software, or more precisely, an application program, or by firmware or hardware. The system may include a memory, such an EEPROM (electronically erasable programmable read only memory) in which are stored the centroid calculation algorithm, the population centroid target and the optimization factors. Memories or storage devices are also provided for storing the unadjusted diagnostic results of patient samples calculated by the analyzer using the pre-set parameters (e.g., optical gain) of the analyzer, the instrument centroid and field population centroid target, and the adjusted or corrected diagnostic patient sample results resulting from the application of the optimization logic. A microprocessor, microcontroller or CPU may be employed to carry out the application of the centroid calculation algorithm to the patient data, compare the field population centroid targets stored in memory to the specific instrument centroid, or make any other comparisons (such as evaluating certain histogram features, for example, the width) to determine if the bias in the instrument centroid values is within the preset limits or ranges, and derive the optimization factor to be applied to the analyzer's pre-set parameters.

The pre-set limits may be derived from certain criteria based on the histogram of the field population; for example, the limits may be based on the 2SD (standard deviation) points of the field population centroid. Thus, if the shape of the reference (field) population centroid is wide, then there is less confidence in the target analyzer's centroid, and the limits (i.e., the threshold outside of which the optimization factor should be applied) should also be widened so as not to over-adjust for noise. Also taken into account in setting the limits may be a consideration of what is diagnostically significant and meaningful. In other words, it is preferable not to set the limits so tight that every diagnostic result must be corrected, and not to set the limits so loose that the optimization factor is never applied.

Field population targets are governed by a set of minimum requirements in order to ensure sufficient data to be representative of the field. For example, a minimum number of individual instruments may be required in order to have enough instrument-to-instrument as well as sample variation. A preferred value for the minimum number of instruments may be about ten, but any value from two or larger could be justified based on the specific application. In addition, for an instrument to be considered for the population centroid, it must have a minimum number of runs performed on that species on that lot. A preferred value for the minimum number of runs per instrument may be about ten, but any value from two or larger could be justified based on the specific application. Access to field population centroid targets could be derived through the use of a web server that aggregates all of the field data and provides the summary or raw data back to the individual applications. The population data could be distributed to the instruments through physical media, electronic delivery (FTP (file transfer protocol) or the like, for example), or through direct contact with the host server. Of course, it should be realized that such structure (e.g., memories, microprocessor and the like) may already exist within the analyzer, and such structure may be conveniently utilized in performing the functions of the automated calibration method of the present invention.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 2 is a histogram comparison for the target data from FIG. 1 compared with a specific instrument running canine samples on the same slide lot used in calculating the centroid of the field population data shown in FIG. 1. FIG. 2A is a graph of an individual instrument response centroid subtracted from the species and lot-specific field population centroid shown in FIG. 1, with frequency of occurrence as the ordinate and the response change, or delta, from the population centroid as the abscissa. FIG. 2B is a graph of the individual instrument response subtracted from the species and lot-specific field population centroid shown in FIG. 1, with frequency of occurrence as the ordinate and the response change, or delta, from the population centroid shown in FIG. 1.

FIG. 3 is a graph of the data in FIG. 2 overlaid with optimization adjusted histogram to show the instrument response to the optimization adjustment and centering of the data to target. More specifically.

DETAILED DESCRIPTION OF THE PREFERRED EMBODIMENTS

Figure 1:
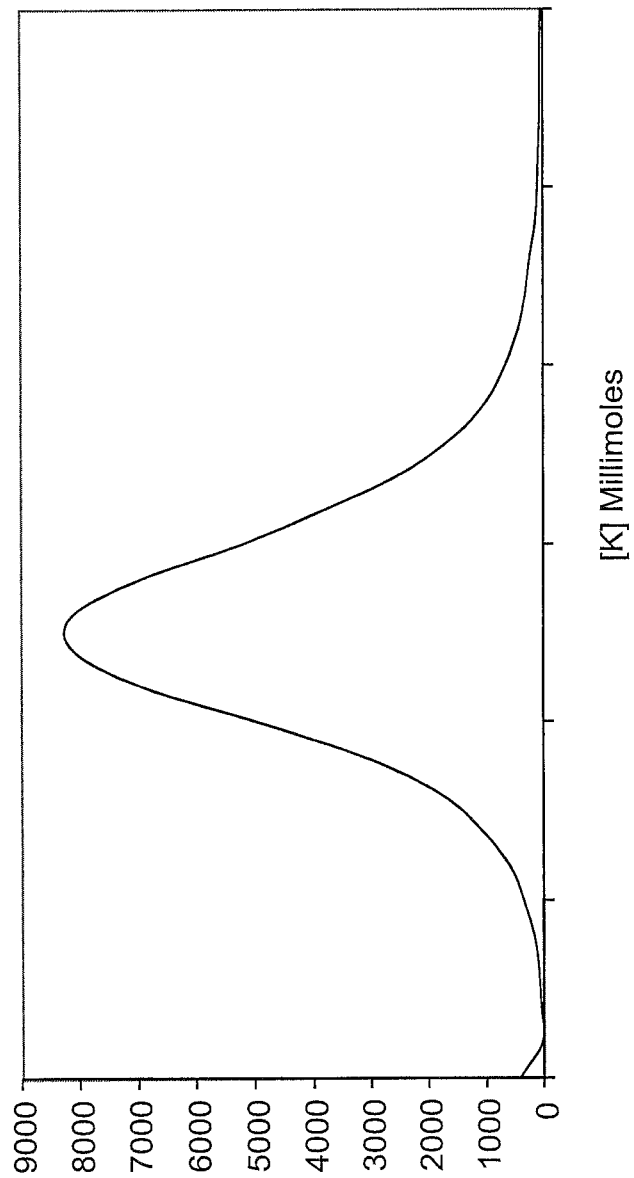
FIG. 1 is an exemplary representative histogram of field population data across greater than 1000 instruments for a single lot of slides (the number of slides tested is 58,988) for a blood chemistry analyzer, specific to canine results for potassium (K) concentration. The representation is in the form of a graph of potassium field data, with frequency of occurrence as the ordinate and concentration as the abscissa, in mMol (millimoles). The maximum concentration occurred at 4.6, and the standard deviation was measured as 0.87. This representation clearly demonstrates the centroid (median) of the histogram as the population target for canine samples on this lot of sample slides.

A preferred form of the method of the present invention, and system implementing the method, will now be described. In accordance with one form of the present invention, an automated method for calibrating in real-time a diagnostic analyzer, such as a blood chemistry analyzer, preferably includes the steps of receiving the diagnostic (e.g., chemistry) results of patient samples calculated by the analyzer using the analyzer's pre-set parameters (such as optical gain, for example), and applying a centroid calculation algorithm (that could manifest as any centrally tending algorithm that identifies the natural center of the data set and could be calculated using average, median, mode, or a more advanced algorithm for finding the center of maximum density) to the patient sample diagnostic results to obtain a centroid (median) value representing the instrument response for a particular species on a particular lot. The method further includes the steps of comparing field population centroid values to the specific instrument centroid values by subtracting one from the other to determine a bias in the centroid of the diagnostic results of the instrument, and comparing the bias from the instrument centroid to the population centroid to limits or ranges which are used to test the extent to which the instrument response resides within such limits or ranges. If the instrument centroid bias falls within the predetermined limits or ranges, then no optimization factor is applied to the patient sample diagnostic results calculated by the analyzer using its pre-set parameters (e.g., optical gain), and the un-optimized patient sample diagnostic results are read out or displayed by the analyzer.

However, should the bias of the instrument centroid fall outside the pre-set limits or ranges during such a comparison, then the method of the present invention further includes the step of applying optimization logic to the instrument based on the population centroid results to obtain adjusted diagnostic results of the patient samples which are now within the acceptable limits or ranges. Such adjusted diagnostic results are read out or displayed by the analyzer and represent a more accurate calculation of the patient sample diagnostic results.

It should be realized that the term "factor" used herein means an adjustment; the optimization factor may be a multiplying factor or an offset, for example.

Furthermore, the automated calibration method includes the steps of deriving from the application of the optimization logic to the instrument results one or more optimization factors, and modifying the calculations performed by the analyzer with its pre-set parameters by the optimization factor (or factors) to correct the results of such calculations without the need to actually change the analyzer's pre-set parameters stored in the analyzer's memory. Thus, for example, by applying the derived optimization factor, the overall gain to the analyzer's optical system may be effectively adjusted from 1.03 to 1.04 to more accurately provide patient sample diagnostic results read out or displayed by the analyzer. Optimization is achieved based on the fundamental operations of the desired analyzer. Automated analyzers commonly have factors associated with reported results that generally function as multipliers or additive offsets. Other mathematical operations can also be used in the optimization logic of the described invention. The optimization approach will determine the ratio of the instrument centroid to the field population centroid and iteratively update the optimization factor and predetermine the instrument centroid. The iteration is complete where the ratio of instrument centroid to field population centroid is minimized at a value of 1 or some other appropriate minimum.

The calibration method is preferably applied each time the diagnostic analyzer generates patient sample results so that the calculated results may be adjusted in real time, and the optimization factor (which is applied to the analyzer's pre-set parameters) may be continually changed as is required, in order to provide more accurate patient readings.

In a more preferred embodiment of the present invention, the centroid algorithm is a median of the patient data. Furthermore, in another preferred form of the invention, the centroid algorithm finds the densest portion of the patient data. In use, particularly when running human analyzers, the user could be alerted that an adjustment is likely needed. The user can then allow the adjustment and follow-up with a control fluid test of the instrument to ensure the adjustment was proper, i.e. before running additional samples. For veterinary applications, adjustments can be made automatically. More specifically, in the veterinary field, targets and ranges are typically species specific, e.g. dogs, cats, horses.

The methods described herein are generally applicable to blood chemistry results which include but are not limited to the following list of parameters: ALT (alanine transferase), AST (aspartate transferase), GGT (gamma-glutamyl transpeptidase), K (potassium), Cl (chloride), Na (sodium), TP (total protein), ALKP (alkaline phosphatase), BUN (blood urea nitrogen), TBIL (total bilirubin), and others. The approach is generally applicable to immunoassay results as well, including but not limited to the following list: T4 (thyroxine), cortisol, bile acids, and others. The approach is generally applicable to hematology results as well, including but not limited to the following list: RBC (red blood cell), MCV (mean corpuscular volume), HGB (hemoglobin), HCT (hematocrit), MCH (mean corpuscular hemoglobin), MCHC (mean corpuscular hemoglobin concentration), PLT (platelet), WBC (white blood cell), RETIC (reticulocyte), NEU neutrophil), LYM (lymphocyte), MONO (monocyte), EOS (eosinophil), BASO (basophil), and others.

One common concern for this type of approach relates to customers that run predominantly ill patients. If a population of patients is ill, then their centroid response could be skewed and might generate an alarm when the instrument is functioning correctly and the responses are appropriately reported. The proposed method mitigates against this concern by requiring multiple instruments and patients in any population for comparisons. The desired implementation and knowledge of the populations will define the minimum sample sizes for a number of instruments and runs per instrument in order to have an appropriate target that is insensitive to specific clinic population biases. For the individual clinic running samples, the approach can be optimized for each customer. A practitioner will know if they are a specialty clinic (oncology practice, for example) and that his or her responses will potentially or probably be biased with respect to the general population of health patients. The system can be optimized for these parameters to handle these conditions.

In accordance with one form of the present invention, an automated method for calibrating in real time a diagnostic analyzer, such as a blood chemistry analyzer, includes the step of receiving diagnostic results of patient samples calculated by the analyzer using the analyzer's pre-set parameters (e.g., optical gain). Then, the central tendency of the patient sample diagnostic results is calculated. Preferably, a centroid calculating algorithm is applied to the diagnostic results to provide an instrument centroid (i.e., the mean or median of the distribution of the instrument's diagnostic results data) as a function of chemical reagent test slide lot and species (e.g., human, equine, feline, canine, and the like). Reagent test slide lots and species should not be intermixed when calculating the centroid of the analyzer diagnostic results. The centroid should be apparent from the data distribution of diagnostic results, which should look like a bell curve, and similar to that shown in FIG. 1 of the drawings, although FIG. 1 shows a field population centroid, as will be explained in greater detail.

The centroid calculation algorithm which is applied to the diagnostic results of patient samples calculated by the analyzer may be any one of many algorithms for calculating a centroid of a data distribution. For example, a moving average algorithm may be applied to the patent sample diagnostic results to calculate the centroid of the analyzer's response. Alternatively, the centroid of the patient sample diagnostic results may be determined by other centroid calculating algorithms, including mean, median, mode, max density and other more elaborate algorithms well known to those skilled in the art.

In accordance with the method of the present invention, the central tendency of a field population of the results of comparable diagnostic analyzers, as a function of the same test reagent lot and species as the diagnostic results of the analyzer being calibrated, is calculated. Again, preferably a centroid of the field population of analyzer results is determined, preferably using a centroid calculating algorithm such as described above. There should be minimum requirements for the number of comparable diagnostic analyzers in the population and the number of runs per analyzer in order to ensure that there exists sufficient data to be representative of the field. For example, a preferred value for the minimum number of instruments may be about ten, but any value from two or larger could be justified based on the specific application. Furthermore, a preferred value for the minimum number of runs per analyzer in the field population may be about ten, but any value from two or larger could be justified based on the specific application. The centroid of the field population of analyzer results should resemble a bell curve, such as shown in the example for potassium (K) concentration field data illustrated by FIG. 1 of the drawings.

With reference to FIG. 1, for an exemplary field population of analyzer results of comparable diagnostic analyzers performing potassium (K) tests using chemical reagent test slides of the same lot, it can be seen that the potassium field data centroid has a mean or median of about 4.5.

In accordance with the method of the present invention, the instrument centroid is compared with the population centroid, and any bias in the instrument centroid is determined from this comparison.

Figure 2B:
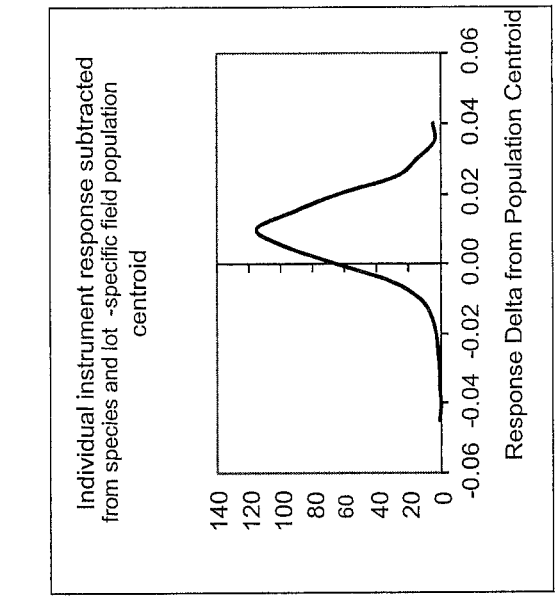
FIG. 2B shows a histogram for an instrument that has a bias to the population target and would be a candidate for optimization. More specifically.
Figure 2A:
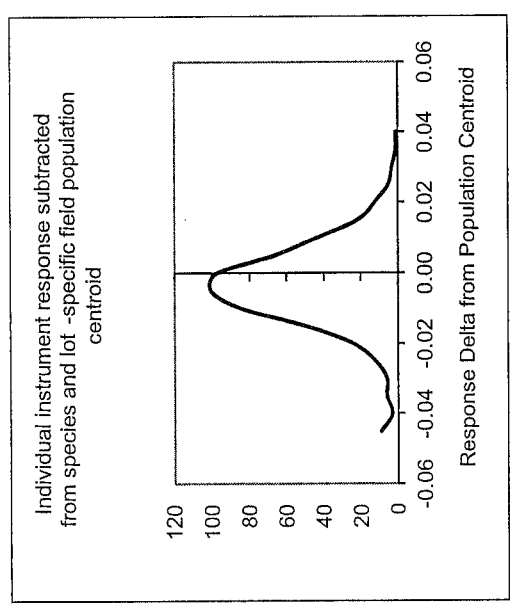
FIG. 2A shows a histogram for an instrument that has minimal bias to the population target and would not be a candidate for optimization (but is nevertheless optimized in FIG. 3A to facilitate an understanding of the invention).

In this regard, reference should be had to FIG. 2 of the drawings. In FIG. 2A, a histogram for an instrument that has a minimal bias, determined from subtracting the individual instrument response centroid from the species and lot-specific field population centroid, is shown. If this bias is within a predetermined range or limits, it is considered minimal and no optimization of the analyzer's diagnostic results of patient samples would be required.

On the other hand, FIG. 2B shows a histogram for a diagnostic analyzer which exhibits a bias determined from subtracting its response centroid from the species and lot-specific field population centroid, such as shown in FIG. 1, which is outside the predetermined range or limits Under such circumstances, the analyzer's diagnostic results of patient samples should be optimized by applying an optimization factor thereto.

More specifically, for diagnostic analyzers that exhibit a bias in their centroid of patient sample diagnostic results, determined from a comparison with the centroid of diagnostic results of a field population of comparable analyzers, an optimization logic is applied to the analyzer's centroid diagnostic results to obtain adjusted diagnostic results of the patient samples which are now within the acceptable limits or range. This optimization logic essentially moves the analyzer's centroid over by a fixed optimization factor applied to the patient sample diagnostic results calculated by the analyzer using its pre-set parameters so that the bias is now minimized or eliminated. For example, the centroid bias shown in FIG. 2A of the analyzer's patient sample diagnostic results, which needed minimal or no optimization, which is also shown in FIG. 3A, has been corrected nevertheless by applying an optimization factor to the analyzer's patient sample diagnostic results to essentially minimize or negate the bias so that the centroid of the diagnostic results of the analyzer substantially coincide with the centroid of the diagnostic results of the field population of comparable analyzers. The optimized centroid diagnostic results are shown in FIG. 3A.

Figure 3B:
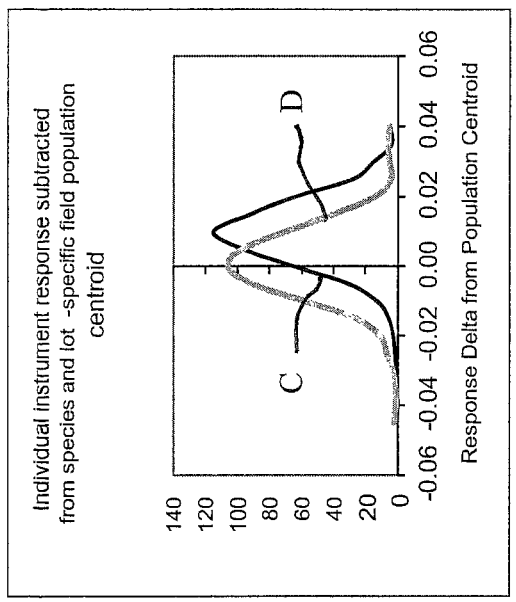
FIG. 3B is a graph of the individual instrument response centroid subtracted from the species and lot-specific field population centroid shown in FIG. 1, taken from FIG. 2B, and an optimized instrument response centroid (subtracted from the field population centroid), with frequency of occurrence as the ordinate and the response change, or delta, from the population centroid as the abscissa. The curve of the individual instrument response centroid subtracted from the field population centroid is designated in FIG. 3B by the reference letter C, and the optimized instrument response centroid (subtracted from the population centroid) is designated in FIG. 3B by reference letter D.
Figure 3A:
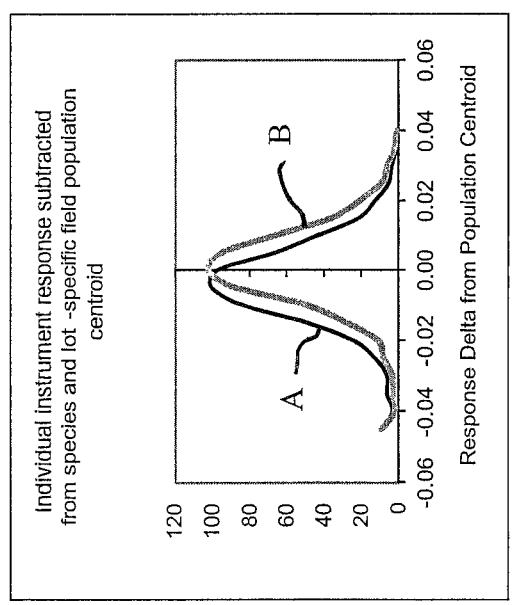
FIG. 3A is a graph of the individual instrument response centroid subtracted from the species and lot-specific field population centroid shown in FIG. 1, taken from FIG. 2A, and an optimized instrument response centroid (subtracted from the field population centroid), with frequency of occurrence as the ordinate and the response change, or delta, from the population centroid as the abscissa. The curve of the individual instrument response centroid subtracted from the field population centroid is designated in FIG. 3A by reference letter A, and the curve of the optimized instrument response centroid (subtracted from the field population centroid) is designated in FIG. 3A by reference letter B.

In FIG. 3B, the bias of the centroid of patient sample diagnostic results of the analyzer shown therein requires optimization, as it falls outside the predetermined range or limits An optimization factor is applied to the patient sample diagnostic results calculated by this analyzer using its pre-set parameters to move the centroid of the analyzer's diagnostic results to be more in line with the median or centroid of the diagnostic results in the field population of comparable analyzers. The optimized centroid of the patient sample diagnostic results of this analyzer is also shown in FIG. 3B. The optimized or adjusted diagnostic results are then read out by the analyzer without the need to change the analyzer's pre-set parameters. Thus, the calculations performed by the analyzer, with its pre-set parameters, are modified using the optimization factor to correct the results of the analyzer's calculations without the need to change the analyzer's pre-set parameters.

The optimization factors are derived from the application of optimization logic to the analyzer's centroid diagnostic results. The optimization logic includes finding the population centroid for the particular lot and animal species being tested and determining the bias from the instrument centroid, and then aggregating over multiple lots for the species to determine a lot-independent bias.

As stated previously, for many chemistry analyzers, the reagent test slides have lots associated with them, and the analyzers have calibration curves associated with each of the lots. Therefore, the response of the chemistry analyzers may be different from one lot to another. A lot-specific field population centroid may be predetermined and used in the calculation of the bias in the diagnostic results for a particular analyzer. Alternatively, the field population centroids of several lots may be aggregated, such as by calculating their differences, or deltas, and the average of the lots, to determine a global field population centroid that is not lot-specific and which may be applied to a particular chemistry analyzer to derive a correction factor for compensating the analyzer's bias in its computation of a diagnostic results. It is preferred to use a global field population centroid rather than a lot-specific field population centroid, since a diagnostic analyzer may run through an entire lot of test slides in about one month.

The derived optimization factor or factors may include multiple patient factors, linear offsets or other mathematical manipulations of the raw data (the diagnostic results) to achieve accurate calibration results.

Figure 4:
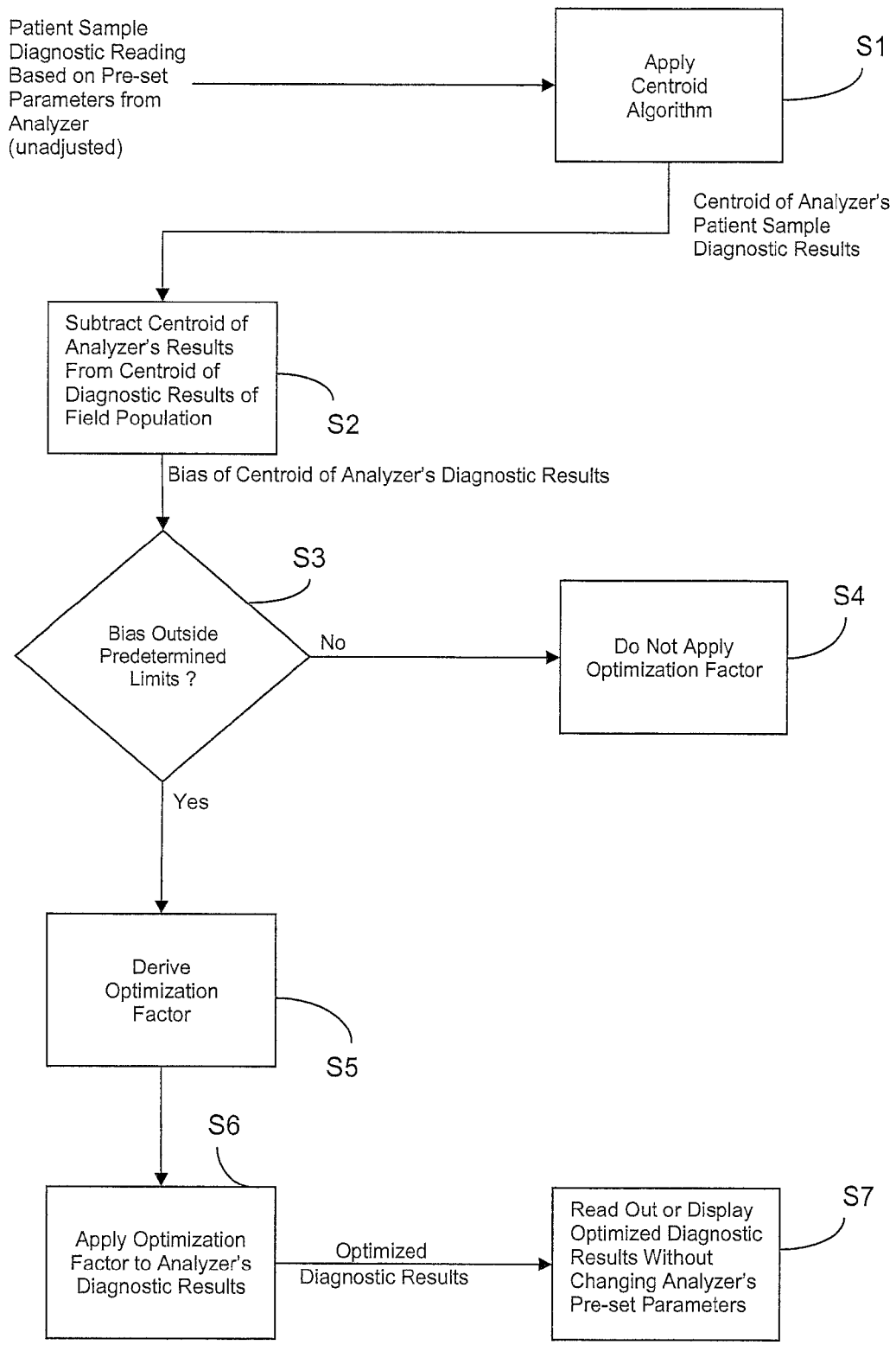
FIG. 4 is a flow chart showing the operation of the system and method of the present invention for real-time, automated calibration of a diagnostic analyzer.

FIG. 4 is a simplified flow chart illustrating the operation of the automated system of the present invention for calibrating a diagnostic analyzer, such as a blood chemistry analyzer. The analyzer calculates the diagnostic results using the analyzer's pre-set parameters (such as optical gain, for example). The patient sample diagnostic readings resulting from the analyzer's calculations based on patient samples are acted upon in a subroutine in which a centroid calculating algorithm is applied (Step S1). This centroid calculation algorithm may be a moving averages algorithm. The result of the application of this algorithm is a centroid of the analyzer's patent sample diagnostic results.

In Step S2, the centroid of the analyzer's patient sample diagnostic results are compared to a centroid of diagnostic results of a field population of comparable analyzers, which may be pre-calculated and stored in the memory of the analyzer. This comparison may be performed by subtracting the centroid of the analyzer's diagnostic results from the centroid of diagnostic results of the field population of comparable analyzers. The result of this comparison is a bias determination of the centroid of diagnostic results of the analyzer (Step S2).

Now, the bias in the centroid of the analyzer's patient sample diagnostic results is compared to a predetermined range or limits (Step S3). If the bias in the centroid of the analyzer's patient sample diagnostic results is within the acceptable limits, then no optimization factor is applied to the analyzer's patient sample diagnostic results (Step S4). However, if the bias in the centroid of the analyzer's patient sample diagnostic results is outside the acceptable limits, then the system and method of the present invention derive or calculate an optimization factor or factors (Step S5). The optimization factor or factors are then applied to the analyzer's patient sample diagnostic results (Step S6) to obtain optimized patient sample diagnostic results. The optimized patient sample diagnostic results, or the un-optimized results if no optimization is required, are read out by the analyzer, and the analyzer's pre-set parameters are not changed (Step S7).

The optimization factor (or factors) is used in modifying the calculations performed by the analyzer with its pre-set parameters to correct the results of such calculations without the need to actually change the analyzer's pre-set parameters stored in the analyzer's memory. Thus, for example, by applying the optimization factor, the overall gain to the analyzer's optical system may be effectively adjusted from 1.03 to 1.04 to more accurately provide patient sample diagnostic results read out or displayed by the analyzer.

The calibration method is preferably applied each time the diagnostic analyzer generates patient sample results so that the calculated results may be automatically adjusted in real time, and the optimization factor (which is applied to the analyzer's pre-set parameters) may be continually changed as is required, in order to provide more accurate patient readings.

Figure 5:
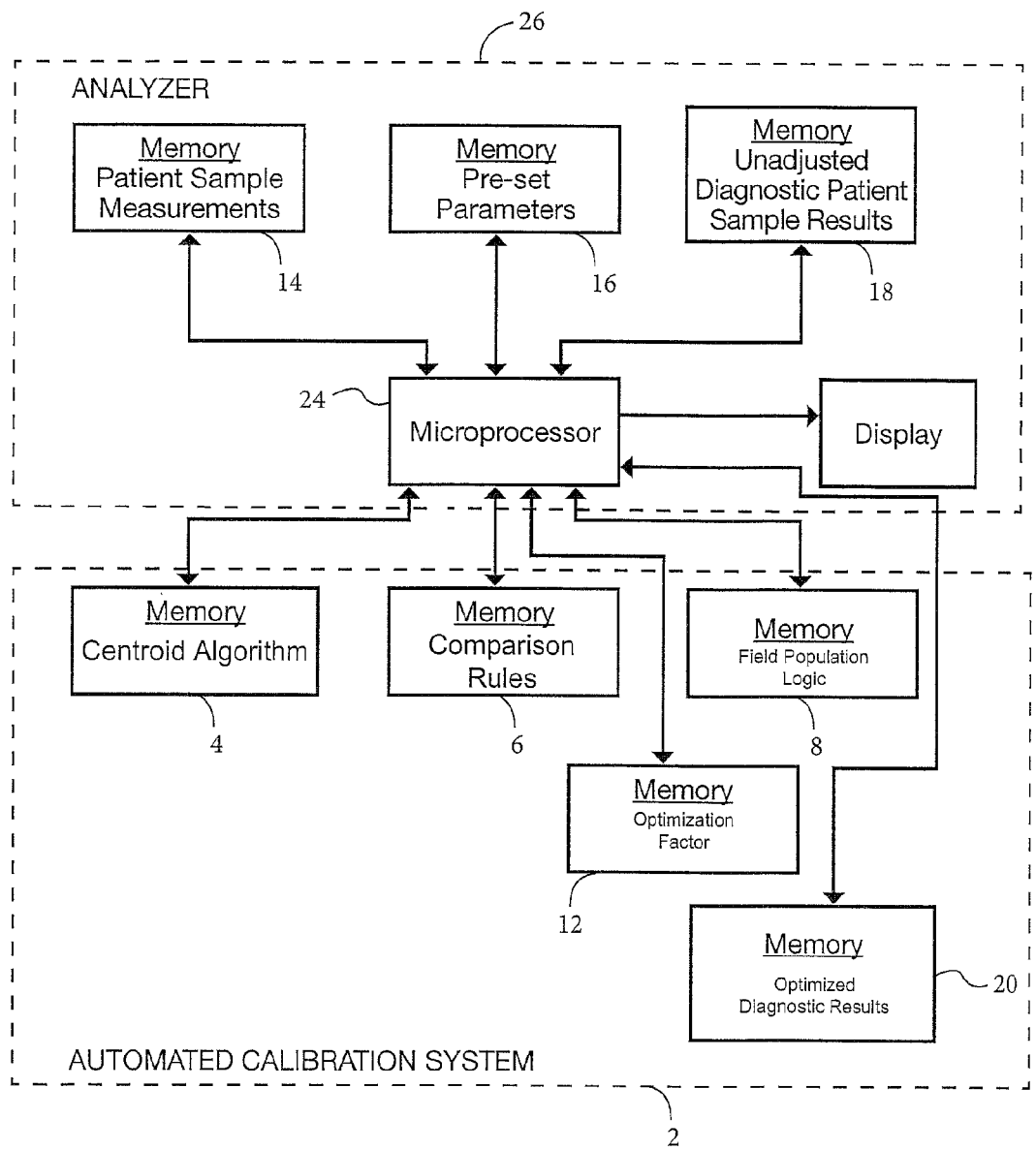
FIG. 5 is a block diagram of an automated system for calibrating a diagnostic analyzer formed in accordance with the present invention, and illustrating the cooperation between the system and the diagnostic analyzer.

FIG. 5 is a block diagram of one form of a system 2 which implements the automated calibration method of the present invention. This system 2 can be realized by software, or more precisely, an application program, or by firmware or hardware. The system 2 may include a memory 4, such as an EEPROM (electronically erasable programmable read only memory) in which is stored the centroid algorithm, a memory 6 in which is stored the comparison rules, a memory 8 in which is stored the field population logic, and a memory 12 in which is stored the optimization factor. Memories or storage devices are also provided for storing patient sample measurements determined by the analyzer (memory 14), the pre-set parameters of the analyzer (memory 16), the unadjusted diagnostic results of patient samples calculated by the analyzer using the pre-set parameters (e.g., optical gain) of the analyzer (memory 18), and the optimized diagnostic results (memory 20) resulting from the application of the comparison logic. A microprocessor, microcontroller or CPU 24 may be employed to carry out the application of the centroid algorithm and comparison logic between the patient data and population target, or make any comparisons to determine if the bias of the instrument centroid is within the limits or ranges, and derive the optimization factor to be applied to the analyzer's pre-set parameters. Of course, it should be realized that such structure (e.g., memories, microprocessor and the like) may already exist within the analyzer 26, and such structure may be conveniently utilized in performing the functions of the automated calibration method of the present invention.

Figure 6:
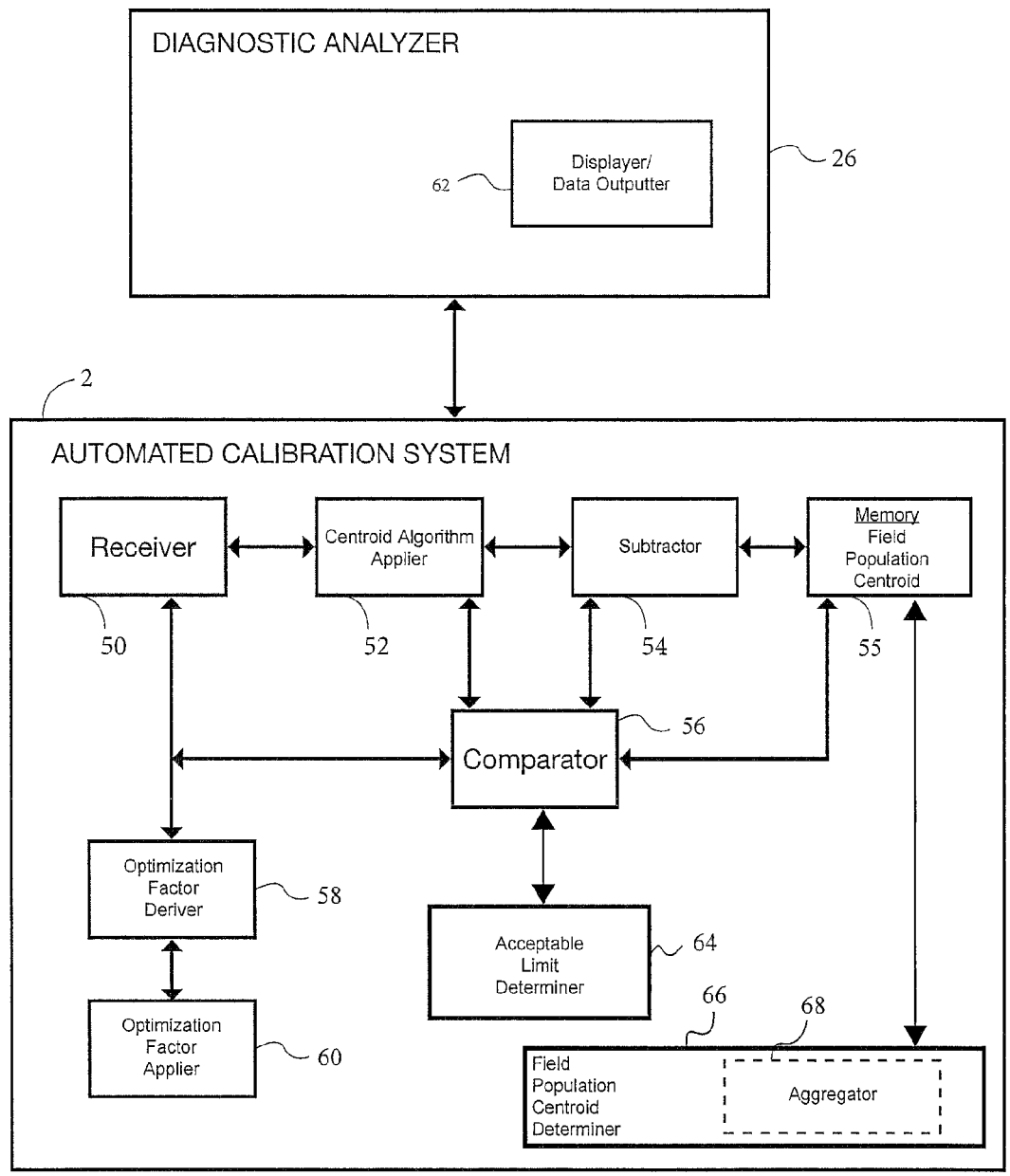
FIG. 6 is a block diagram of an alternative embodiment of an automated system for calibrating a diagnostic analyzer formed in accordance with the present invention, and illustrating the cooperation between the system and the diagnostic analyzer.

FIG. 6 is a block diagram of a second form of a system 2 which implements the automatic calibration method of the present invention. The automated system calibrates in real time a diagnostic analyzer 26, where the diagnostic analyzer performs calculations on patient diagnostic samples using pre-set parameters. Preferably, the automated calibration system includes a receiver 50 which receives diagnostic results of patient samples calculated by the analyzer using the pre-set parameters of the analyzer. A centroid algorithm applier 52 applies a centroid calculation algorithm to the patient sample diagnostic results of the analyzer to obtain a centroid of the analyzer's patient sample diagnostic results. A subtractor of centroids 54 receives the centroid of the analyzer's diagnostic results, and subtracts the centroid from a centroid of diagnostic results of a field population of comparable analyzers, which may be stored in a memory of the analyzer. The centroid subtractor 54 thus determines a bias in the centroid of the analyzer's diagnostic results. This bias is provided to a bias comparator 56, which compares the bias to a predetermined acceptable range or limits. If the bias comparator 56 determines that the bias of the centroid of the analyzer's diagnostic results is within the acceptable limits, then no optimization factor is applied to the analyzer's diagnostic results. However, if the bias comparator 56 determines that the bias is outside the predetermined range or limits, then an optimization factor will be applied to the analyzer's diagnostic results which, effectively, will move the centroid of the diagnostic results of the analyzer more in line with the centroid of the diagnostic results of the field population of comparable analyzers and within the acceptable range or limits.

The system may further include an optimization factor calculator 58. The optimization factor calculator 58 derives from the application of optimization logic to the analyzer's centroid diagnostic results one or more optimization factors. The optimization factor or factors may be based on the extent or degree of deviation of the analyzer's centroid of patient sample diagnostic results from the field population centroid. A greater degree of deviation may require the application of an optimization factor having a relatively greater offset or multiplier. Alternatively, the same predetermined optimization factor may be applied not based on the degree of deviation but rather in most or all instances where the bias of the centroid of the patient sample diagnostic results exceeds the predetermined acceptable limits or threshold.

The system further includes an optimization factor applier 60, which applies the optimization factor or factors to the analyzer's diagnostic results, and obtains therefrom optimized diagnostic results. The optimized diagnostic results, or the un-optimized results if no optimization is required, are displayed or read out, or provided, on a display or data outputter 62.

Although in a preferred form of the present invention the bias in the centroid of the patient sample diagnostic results of the analyzer are compared to predetermined acceptable limits, it is envisioned to be within the scope of the present invention to have the system determine such acceptable limits. Accordingly, the automated system may further include an acceptable limit determiner 64 which determines the acceptable limits by calculating, for example, the standard deviation of the centroid of diagnostic results of the field population of comparable analyzers.

Furthermore, the automated system of the present invention may include a field population centroid determiner 66 which determines the centroid of diagnostic results of the field population of comparable analyzers. The field population of diagnostic results used by the field population centroid determiner 66 may be limited to a specific lot of samples to derive a centroid of a lot-specific field population of diagnostic results of comparable analyzers. This centroid of the lot-specific field population of diagnostic results of comparable analyzers is compared with the centroid of the patient sample diagnostic results of the analyzer to determine the bias in the centroid of the patient sample diagnostic results of the analyzer.

Alternatively, the field population used by the field population centroid determiner 66 includes diagnostic results from a plurality of sample lots. In such an embodiment, the field population centroid determiner 66 has an aggregator 68 which aggregates the diagnostic results of the plurality of sample lots, thereby deriving a centroid of a global field population of diagnostic results of comparable analyzers. The centroid of the global field population of diagnostic results of comparable analyzers is compared with the centroid of the patient sample diagnostic results of the analyzer to determine the bias in the centroid of the patient sample diagnostic results of the analyzer.

Automated diagnostic analyzers, such as blood chemistry analyzers, can have their accuracy improved and bias reduced in accordance with the system and method of the present invention utilizing population statistics with centroid calculations. A simple split sample comparison with a reference analyzer or comparison with a control material can verify proper adjustments to the analyzer's settings and ensure accuracy. The system and method of the present invention are quite useful with veterinary analyzers and in veterinary offices, where control fluid costs are prohibitive to their regular use, and many are based on human fixed cells requiring different algorithms than used with patient samples.

The system and method of the present invention will make the adjustments, as required, to the calculations performed by the analyzer, in real time, without the need for the clinician to make adjustments to the analyzer manually based on the clinician's interpretation of graphs and other data presented on a display of the analyzer, thereby minimizing or eliminating errors in the clinician's analysis or his possibly overcorrecting a perceived instrumentation bias.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An automated method for calibrating in real time a diagnostic analyzer, which comprises the steps of:
   receiving diagnostic results of patient samples calculated by the analyzer using pre-set parameters of the analyzer;
   calculating a centroid of the patient sample diagnostic results of the analyzer;
   comparing the centroid of the patient sample diagnostic results of the analyzer with a centroid of actual patient sample diagnostic results of a field population of comparable analyzers to determine a bias in the centroid of the patient sample diagnostic results of the analyzer;
   comparing the bias in the centroid of the patient sample diagnostic results of the analyzer with predetermined acceptable limits;
   if the bias of the centroid of the patient sample diagnostic results of the analyzer falls within the predetermined acceptable limits, then not applying an optimization factor to the patient sample diagnostic results calculated by the analyzer using the pre-set parameters of the analyzer;
   if the bias of the centroid of the patient sample diagnostic results of the analyzer falls outside the predetermined acceptable limits, then applying the optimization factor to the patient sample diagnostic results of the analyzer to obtain optimized patient sample diagnostic results; and
   outputting the optimized or un-optimized patient sample diagnostic results by the analyzer.

2. An automated method for calibrating in real time a diagnostic analyzer as defined by claim 1, which further comprises the step of calculating the centroid of actual patient sample diagnostic results of a field population of comparable analyzers, wherein the centroid of the actual patient sample diagnostic results of the field population of comparable analyzers is calculated using certain selected species of animals, and wherein the centroid of the patient sample diagnostic results of the analyzer is derived using the same certain species of animals as the certain species of animals used for the field population.

3. An automated method for calibrating in real time a diagnostic analyzer as defined by claim 1, wherein the diagnostic analyzer is one of a hemotology analyzer and a chemistry analyzer.

4. An automated method for calibrating in real time a diagnostic analyzer as defined by claim 3, wherein the diagnostic analyzer is a blood chemistry analyzer.

5. An automated method for calibrating in real time a diagnostic analyzer as defined by claim 1, which further comprises the step of:
   determining the acceptable limits by calculating the standard deviation of the centroid of actual patient sample diagnostic results of the field population of comparable analyzers.

6. An automated method for calibrating in real time a diagnostic analyzer as defined by claim 1, which further comprises the step of:
   determining the centroid of actual patient sample diagnostic results of the field population of comparable analyzers.

7. An automated method for calibrating in real time a diagnostic analyzer as defined by claim 1, which further comprises the step of:
   determining the centroid of actual patient sample diagnostic results of the field population of comparable analyzers, the field population of diagnostic results used in determining the centroid of actual patient sample diagnostic results being limited to a specific lot of actual patient samples thereby deriving a centroid of a lot-specific field population of actual patient sample diagnostic results of comparable analyzers, the centroid of the lot-specific field population of actual patient sample diagnostic results of comparable analyzers being compared with the centroid of the patient sample diagnostic results of the analyzer to determine the bias in the centroid of the patient sample diagnostic results of the analyzer.

8. An automated method for calibrating in real time a diagnostic analyzer as defined by claim 1, which further comprises the step of:
   determining the centroid of actual patient sample diagnostic results of the field population of comparable analyzers, the field population of diagnostic results used in determining the centroid of actual patient sample diagnostic results including diagnostic results from a plurality of actual patient sample lots, the determining step including the sub-step of aggregating the diagnostic results of the plurality of actual patient sample lots, thereby deriving a centroid of a global field population of actual patient sample diagnostic results of comparable analyzers, the centroid of the global field population of actual patient sample diagnostic results of comparable analyzers being compared with the centroid of the patient sample diagnostic results of the analyzer to determine the bias in the centroid of the patient sample diagnostic results of the analyzer.

9. An automated system for calibrating in real time a diagnostic analyzer, the diagnostic analyzer performing calculations on patient diagnostic samples using pre-set parameters of the analyzer, which comprises:
   one or more memories in which are stored a centroid algorithm for calculating a centroid of patient sample diagnostic results of the analyzer, a centroid of actual patient sample diagnostic results of a field population of comparable analyzers, logic to compare the analyzer and field population centroids, predetermined acceptable limits and an optimization factor;
   a microprocessor operatively coupled to the one or more memories, the microprocessor calculating the centroid of the patient sample diagnostic results of the analyzer, comparing the centroid of the patient sample diagnostic results of the analyzer with the centroid of actual patient sample diagnostic results of the field population of comparable analyzers and determining therefrom a bias in the centroid of the patient sample diagnostic results of the analyzer, comparing the bias in the centroid of the patient sample diagnostic results of the analyzer with the predetermined acceptable limits, not applying the optimization factor to the patient sample diagnostic results calculated by the analyzer using the pre-set parameters if the bias of the centroid of the patient sample diagnostic results of the analyzer falls within the predetermined acceptable limits, and applying the optimization factor to the patient sample diagnostic results calculated by the analyzer if the bias of the centroid of the patient sample diagnostic results of the analyzer falls outside the predetermined acceptable limits, and obtaining optimized patient sample diagnostic results; and
   an outputter for outputting the optimized or un-optimized patient sample diagnostic results.

10. An automated system for calibrating in real time a diagnostic analyzer as defined by claim 9, wherein the diagnostic analyzer is one of a hemotology analyzer and a chemistry analyzer.

11. An automated system for calibrating in real time a diagnostic analyzer as defined by claim 9, wherein the diagnostic analyzer is a blood chemistry analyzer.

12. An automated system for calibrating in real time a diagnostic analyzer, the diagnostic analyzer performing calculations on patient diagnostic samples using pre-set parameters of the analyzer, which comprises:
   means for receiving diagnostic results of patient samples calculated by the analyzer using the pre-set parameters of the analyzer;
   means for calculating a centroid of the patient sample diagnostic results of the analyzer;
   means for comparing the centroid of the patient sample diagnostic results of the analyzer with a centroid of actual patient sample diagnostic results of a field population of comparable analyzers to determine a bias in the centroid of the patient sample diagnostic results of the analyzer;
   means for comparing the bias in the centroid of the patient sample diagnostic results of the analyzer with predetermined acceptable limits;
   means for applying an optimization factor to the patient sample diagnostic results of the analyzer if the bias of the centroid of the patient sample diagnostic results of the analyzer is outside the predetermined acceptable limits and thereby obtaining optimized patient sample diagnostic results, and not applying the optimization factor to the patient sample diagnostic results of the analyzer if the bias of the centroid of the patient sample diagnostic results of the analyzer falls within the predetermined acceptable limits; and
   means for outputting the optimized or un-optimized patient sample diagnostic results by the analyzer.

13. An automated system for calibrating in real time a diagnostic analyzer as defined by claim 12, which further comprises:
    means for calculating the centroid of actual patient sample diagnostic results of the field population of comparable analyzers.

14. An automated system for calibrating in real time a diagnostic analyzer as defined by claim 12, which further comprises:
    means for calculating the centroid of actual patient sample diagnostic results of the field population of comparable analyzers, wherein the field population of diagnostic results used by the centroid calculating means in determining the centroid of actual patient sample diagnostic results is limited to a specific lot of samples thereby deriving a centroid of a lot-specific field population of actual patient sample diagnostic results of comparable analyzers, the centroid of the lot-specific field population of actual patient sample diagnostic results of comparable analyzers being compared with the centroid of the patient sample diagnostic results of the analyzer to determine the bias in the centroid of the patient sample diagnostic results of the analyzer.

15. An automated system for calibrating in real time a diagnostic analyzer as defined by claim 12, which further comprises:
    means for calculating the centroid of actual patient sample diagnostic results of the field population of comparable analyzers, wherein the field population of diagnostic results used by the centroid calculating means in determining the centroid of actual patient sample diagnostic results includes diagnostic results from a plurality of actual patient sample lots, the centroid calculating means further having aggregating means which aggregates the diagnostic results of the plurality of actual patient sample lots, thereby deriving a centroid of a global field population of actual patient sample diagnostic results of comparable analyzers, the centroid of the global field population of actual patient sample diagnostic results of comparable analyzers being compared with the centroid of the patient sample diagnostic results of the analyzer to determine the bias in the centroid of the patient sample diagnostic results of the analyzer.

16. An automated system for calibrating in real time a diagnostic analyzer as defined by claim 12, which further comprises:
    means for determining the acceptable limits, the acceptable limit determining means calculating the standard deviation of the centroid of actual patient sample diagnostic results of the field population of comparable analyzers.

17. An automated system for calibrating in real time a diagnostic analyzer, the diagnostic analyzer performing calculations on patient diagnostic samples using pre-set parameters of the analyzer, which comprises:
    a receiver which receives diagnostic results of patient samples calculated by the analyzer using the pre-set parameters of the analyzer;
    a centroid algorithm applier which applies a centroid calculating algorithm to the patient sample diagnostic results of the analyzer and calculating therefrom a centroid of the patient sample diagnostic results of the analyzer;
    a subtractor which subtracts the centroid of the patient sample diagnostic results of the analyzer from a centroid of actual patient sample diagnostic results of a field population of comparable analyzers and determining therefrom a bias in the centroid of the patient sample diagnostic results of the analyzer;
    a comparator which compares the bias in the centroid of the patient sample diagnostic results of the analyzer with predetermined acceptable limits;
    an optimization factor deriver which derives an optimization factor;
    an optimization factor applier which applies the optimization factor to the patient sample diagnostic results of the analyzer if the bias of the centroid of the patient sample diagnostic results of the analyzer falls outside the predetermined acceptable limits, and which does not apply the optimization factor to the patient sample diagnostic results of the analyzer if the bias of the centroid of the patient sample diagnostic results of the analyzer falls within the predetermined acceptable limits; and
    a displayer which displays the optimized or un-optimized patient sample diagnostic results by the analyzer.

18. An automated system for calibrating in real time a diagnostic analyzer, as defined by claim 17, which further comprises:
    an acceptable limit determiner which determines the acceptable limits by calculating the standard deviation of the centroid of actual patient sample diagnostic results of the field population of comparable analyzers.

19. An automated system for calibrating in real time a diagnostic analyzer, as defined by claim 17, which further comprises:
    a field population centroid determiner which determines the centroid of actual patient sample diagnostic results of the field population of comparable analyzers.

20. An automated system for calibrating in real time a diagnostic analyzer, as defined by claim 17, which further comprises:
    a field population centroid determiner which determines the centroid of actual patient sample diagnostic results of the field population of comparable analyzers, wherein the field population of diagnostic results used by the determiner in determining the centroid of actual patient sample diagnostic results is limited to a specific lot of actual patient samples thereby deriving a centroid of a lot-specific field population of actual patient sample diagnostic results of comparable analyzers, the centroid of the lot-specific field population of actual patient sample diagnostic results of comparable analyzers being compared with the centroid of the patient sample diagnostic results of the analyzer to determine the bias in the centroid of the patient sample diagnostic results of the analyzer.

21. An automated system for calibrating in real time a diagnostic analyzer, as defined by claim 17, which further comprises:
    a field population centroid determiner which determines the centroid of actual patient sample diagnostic results of the field population of comparable analyzers, wherein the field population of diagnostic results used by the determiner in determining the centroid of actual patient sample diagnostic results includes diagnostic results from a plurality of actual patient sample lots, the field population centroid determiner having an aggregator which aggregates the diagnostic results of the plurality of actual patient sample lots, thereby deriving a centroid of a global field population of actual patient sample diagnostic results of comparable analyzers, the centroid of the global field population of actual patient sample diagnostic results of comparable analyzers being compared with the centroid of the patient sample diagnostic results of the analyzer to determine the bias in the centroid of the patient sample diagnostic results of the analyzer.

\* \* \* \* \*